US008515546B2

(12) United States Patent
Goddard et al.

(10) Patent No.: US 8,515,546 B2
(45) Date of Patent: Aug. 20, 2013

(54) METHOD AND APPARATUS FOR CONTROLLING STIMULATION PULSES DURING THE PROGRAMMING OF AN IMPLANTABLE PULSE GENERATOR

(75) Inventors: Crystal Goddard, McKinney, TX (US); Jason Pounds, Frisco, TX (US); Tom Younker, McKinney, TX (US); Karen Overton, Plano, TX (US); Jonathan Avedikian, Plano, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 0 days.

(21) Appl. No.: 13/618,705

(22) Filed: Sep. 14, 2012

(65) Prior Publication Data

US 2013/0172956 A1 Jul. 4, 2013

Related U.S. Application Data

(60) Provisional application No. 61/580,886, filed on Dec. 28, 2011.

(51) Int. Cl.
*A61N 1/00* (2006.01)
(52) U.S. Cl.
USPC ............................................... 607/59

(58) Field of Classification Search
USPC ............................................... 607/59
See application file for complete search history.

(56) References Cited

U.S. PATENT DOCUMENTS

| 6,393,325 B1 * | 5/2002 | Mann et al. ............. 607/46 |
| 7,519,431 B2 | 4/2009 | Goetz et al. |
| 7,957,814 B2 | 6/2011 | Goetz et al. |
| 7,974,703 B2 | 7/2011 | Goetz et al. |
| 2009/0326608 A1 | 12/2009 | Huynh et al. |

* cited by examiner

*Primary Examiner* — George Manuel
*Assistant Examiner* — Robert N Wieland

(57) ABSTRACT

In one embodiment, a method for the controlling of the stimulation pulses being delivered via electrodes to a patient during the programming of a pulse generator using a controller device and selecting of a minimum amplitude that corresponds to the minimum amplitude for which the patient can detect stimulation; selecting an electrode combination defined in the controller device; setting the stimulation amplitude; making a determination of the amplitude for the stimulation pulses is greater than the perception amplitude, and if so, changing the amplitude of the stimulation pulses to be less than or equal to the perception amplitude; and if not or subsequent to the changing of the amplitude, changing the selected one of a plurality of electrode combinations to a different combination.

12 Claims, 8 Drawing Sheets

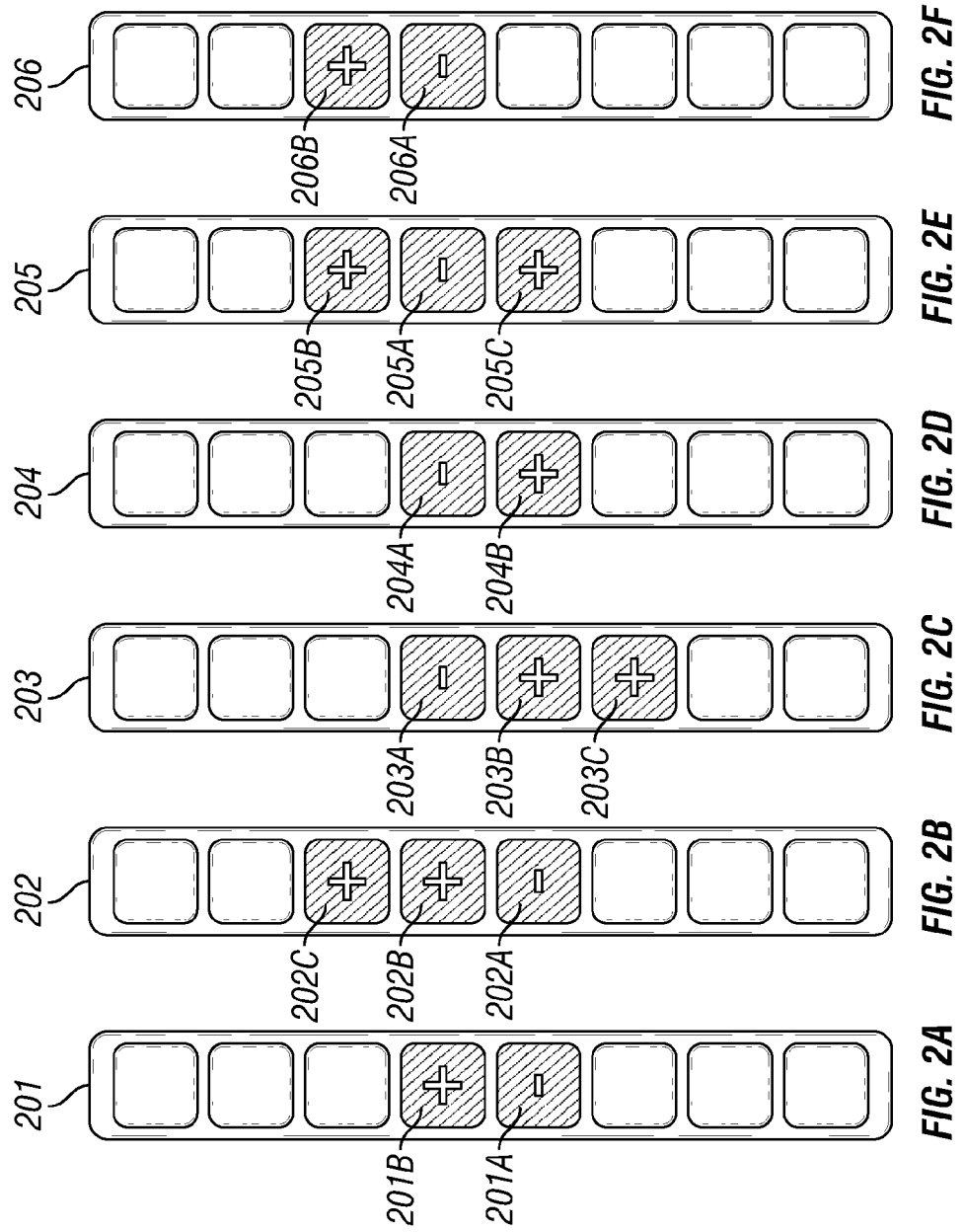

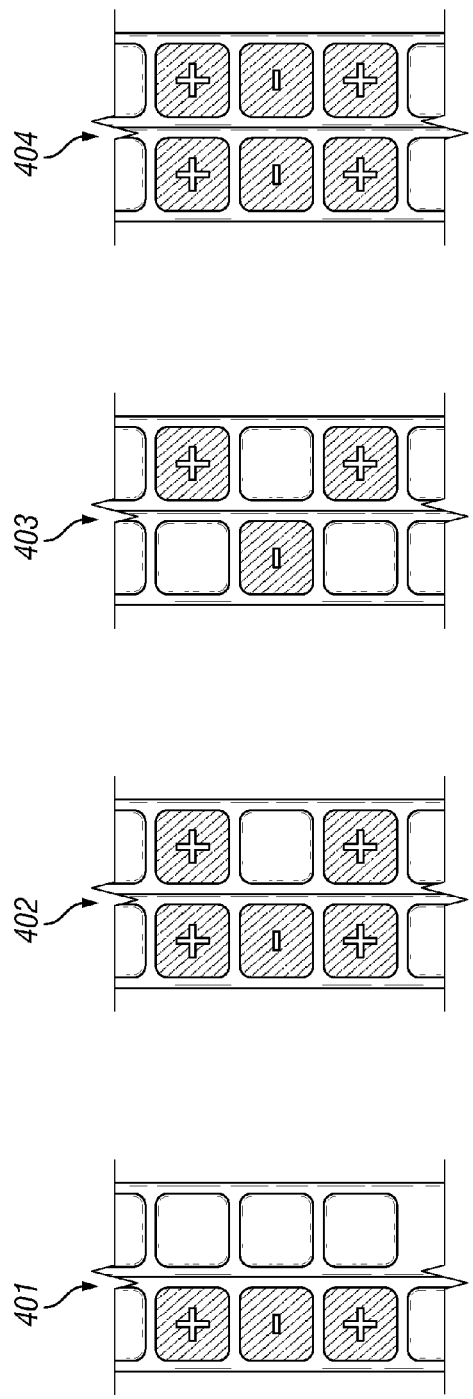
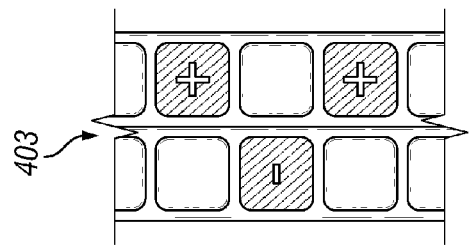
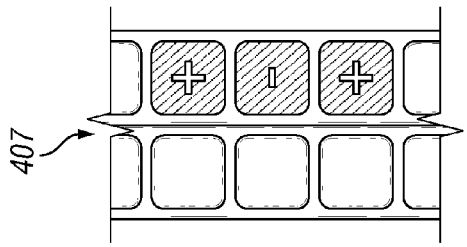
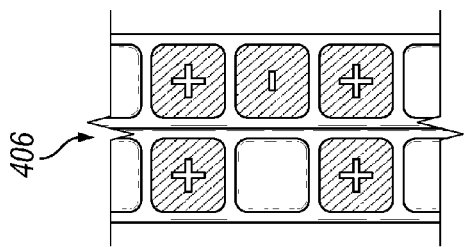
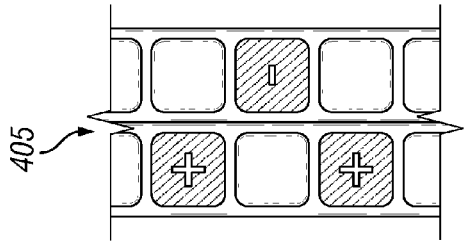

METHOD AND APPARATUS FOR CONTROLLING STIMULATION PULSES DURING THE PROGRAMMING OF AN IMPLANTABLE PULSE GENERATOR

TECHNICAL FIELD

The present application is generally directed to a method and apparatus for controlling an implantable pulse generator to provide electrical stimulation therapy to a patient by successively controlling the amplitude of the generated pulse when shifting a locus of electrical stimulation.

BACKGROUND

Neurostimulation systems are devices that generate electrical pulses and deliver the pulses to nerve tissue to treat a variety of disorders. Neurostimulation systems generally include a pulse generator and one or more leads. The pulse generator is typically implemented using a metallic housing that encloses circuitry for generating the electrical pulses, control circuitry, communication circuitry, a rechargeable battery, etc. The pulse generation circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on a stimulation lead.

Spinal cord stimulation (SCS) is an example of neurostimulation in which electrical pulses are delivered to nerve tissue in the spine typically for the purpose of chronic pain control. Other examples include deep brain stimulation, cortical stimulation, cochlear nerve stimulation, peripheral nerve stimulation, vagal nerve stimulation, sacral nerve stimulation, etc. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue. Specifically, applying electrical energy to the spinal cord associated with regions of the body afflicted with chronic pain to effectively mask the transmission of non-acute pain sensations to the brain.

Also, each exterior region, or each dermatome, of the human body is associated with a particular spinal nerve root at a particular longitudinal spinal position. The head and neck regions are associated with C2-C8, the back region extends from C2-S3, the central diaphragm is associated with spinal nerve roots between C3 and C5, the upper extremities correspond to C5 and T1, the thoracic wall extends from T1 to T11, the peripheral diaphragm is between T6 and T11, the abdominal wall is associated with T6-L1, lower extremities are located from L2 to S2, and the perineum from L4 to S4. In conventional neurostimulation, when a patient experiences pain in one of these regions, a neurostimulation lead is implanted adjacent to the spinal cord at the corresponding spinal position. By example, to address chronic pain sensations that commonly focus on the lower back and lower extremities using conventional techniques, a specific energy field is typically applied to a region between vertebrae levels T8 and T12.

Positioning of an applied electrical field relative to a physiological midline is also important. Nerve fibers extend between the brain and a nerve root along the same side of the dorsal column as the peripheral areas the fibers represent. Pain that is concentrated on only one side of the body is "unilateral" in nature. To address unilateral pain, electrical energy is applied to neural structures on the side of a dorsal column that directly corresponds to a side of the body subject to pain. Pain that is present on both sides of a patient is "bilateral." Accordingly, bilateral pain is addressed through application of electrical energy along both sides of the column and/or along a patient's physiological midline.

Accordingly, at any particular vertebral level, it is possible to stimulate a number of nerve fibers and structures of the spinal cord and, thereby cause the patient to experience paresthesia over several areas of the patient's body. Clinicians typically attempt to define a neurostimulation therapy by stimulating nerve fibers associated with locations of chronic pain while excluding nerve fibers associated with non-afflicted locations. To define an acceptable neurostimulation therapy, a clinician selects values for a number of programmable parameters. For example, the clinician may select parameters defining pulse amplitude, pulse width, and pulse frequency. The clinician may also select electrode polarities for delivery of the pulses. The process of selecting values for the parameters can be time consuming and may require a great deal of trial and error before an acceptable therapeutic program is identified. In many cases, the clinician may need to test various electrode combinations and parameters to achieve the optimal stimulation. The clinician may record notes on the efficacy and side effects of each combination after delivery of stimulation via that combination. In this manner, the clinician is able to later compare and select from the tested combinations.

SUMMARY

Exemplary embodiments provide a method for the controlling of the stimulation pulses being delivered via a plurality of electrodes to tissue of a patient during the programming of a pulse generator using a controller device by a user. The method includes the selecting of a perception amplitude that corresponding to the minimum amplitude of the stimulation pulses for which the patient can detect stimulation; selecting one of a plurality of electrode combinations defined in the controller device; setting the amplitude for the stimulation pulses to be applied to the electrodes of the selected electrode combination; receiving input from the user to change the selected one of the plurality of electrode combinations to a different one of the plurality of electrode combinations; making a determination of the amplitude for the stimulation pulses is greater than the perception amplitude, and if the determination is positive, automatically changing the amplitude of the stimulation pulses to be less than or equal to the perception amplitude; and if the determination is negative or subsequent to the changing of the amplitude for the stimulation pulses to be less than or equal to the perception amplitude, changing the selected one of a plurality of electrode combinations to the different one of the plurality of electrode combinations.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims.

The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWINGS

FIGS. 2A-2F depict a stimulation lead in which different electrode combinations are applied to electrodes of the lead to gradually shift the locus of stimulation longitudinally in a direction parallel to the longitudinal axis of the lead.

FIGS. 4A-4G respectively depict electrode combinations that gradually shift the locus of stimulation from left to right between two columns of electrodes formed by two stimulation leads.

DETAILED DESCRIPTION

Figure 1:
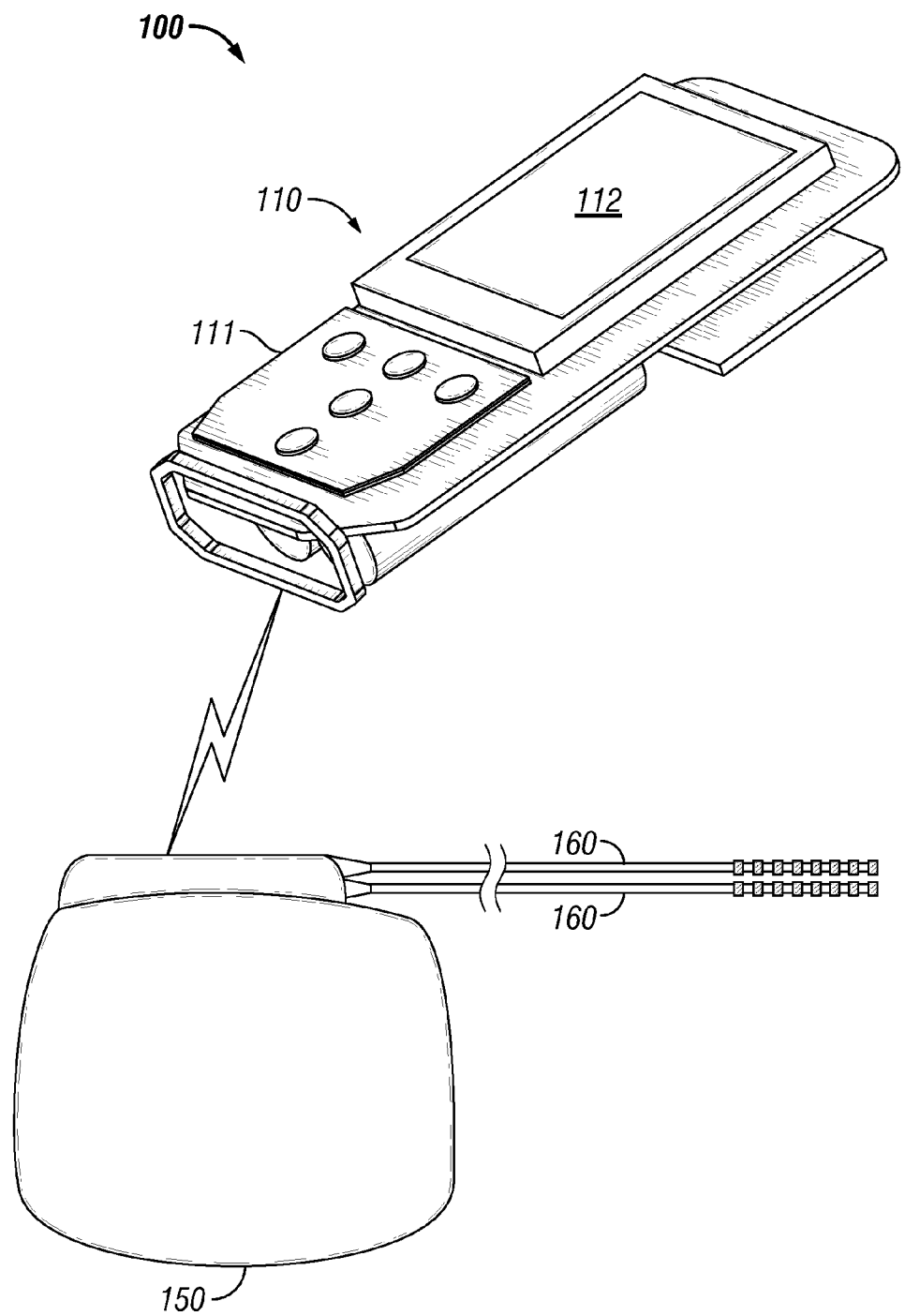
FIG. 1 depicts a medical device system including a controller for controlling an implantable pulse generator according to one representative embodiment.
Figure 3H:
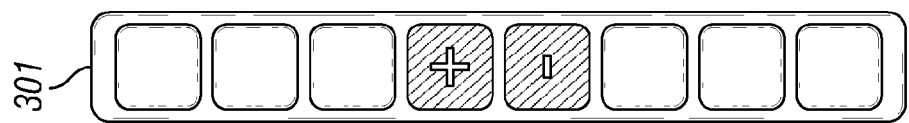
FIGS. 3A-3H depict another set of electrode combinations in which seven unique electrode combinations are utilized to translate the locus of stimulation longitudinally along a column of electrodes.
Figure 3G:
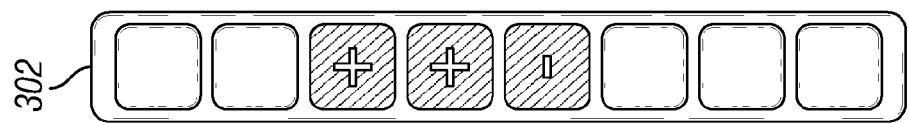
Figure 3F:
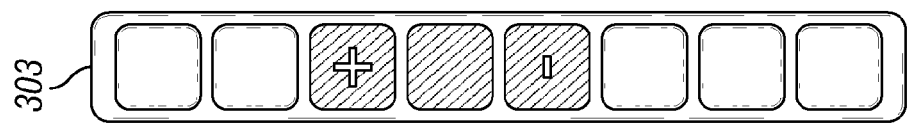
Figure 3E:
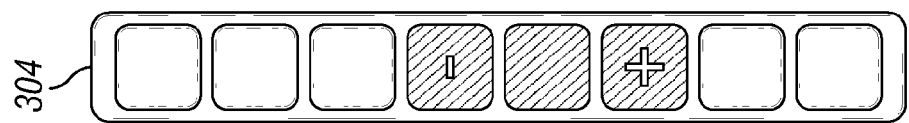
Figure 3D:
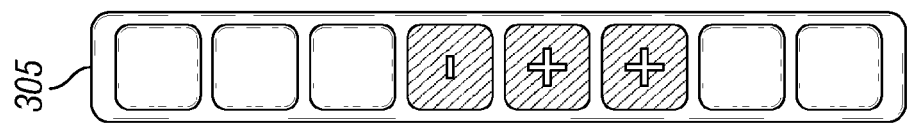
Figure 3C:
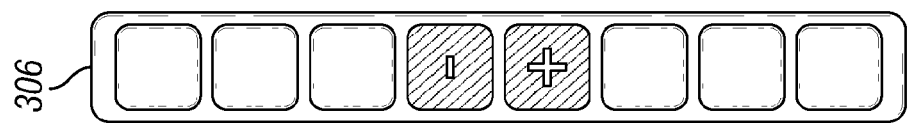
Figure 3B:
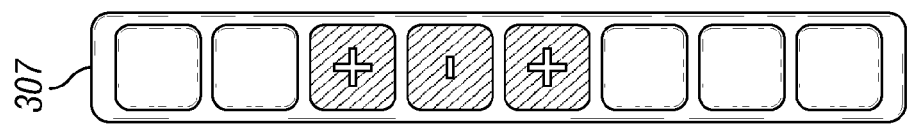
Figure 3A:
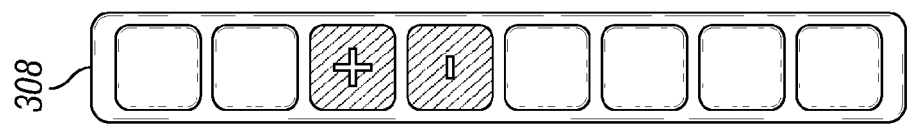

FIG. 1 depicts medical device system 100 including controller 110 for controlling implantable pulse generator 150 according to one representative embodiment. Pulse generator 150 may be adapted to generate electrical pulses to treat any number of neurological diseases or conditions. Pulse generator 150 can be implanted at any suitable location within a patient such as the lower abdominal region, lower back region, sub-clavicle region, etc.

Implantable pulse generator 150 typically comprises a metallic housing that encloses pulse generating circuitry, control circuitry, communication circuitry, battery, etc. of the device. An example of pulse generating circuitry is described in U.S. Patent Publication No. 20060170486 entitled "PULSE GENERATOR HAVING AN EFFICIENT FRACTIONAL VOLTAGE CONVERTER AND METHOD OF USE," which is incorporated herein by reference. A microprocessor and associated charge control circuitry for an implantable pulse generator is described in U.S. Patent Publication No. 20060259098, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. patent Ser. No. 11/109,114, entitled "IMPLANTABLE DEVICE AND SYSTEM FOR WIRELESS COMMUNICATION," which is incorporated herein by reference. An example of a commercially available implantable pulse generator is the EON® pulse generator available from Advanced Neuromodulation Systems, Inc. Although an implantable pulse generator is described according to some embodiments, other pulse generators could be similarly programmed. For example, an external trial stimulator may be programmed according to alternative embodiments.

One or more stimulation leads 160 are electrically coupled to the pulse generating circuitry of pulse generator 150, e.g., through the electrical contacts of the header of pulse generator 150 or through a lead extension device. As shown in FIG. 1, the two stimulation leads stimulation leads, although any 160 are percutaneous suitable type of stimulation lead can be employed. Examples of commercially-available stimulation leads are the Octrode® percutaneous lead and the LAMITRODE TRIPOLE 8™ paddle lead available from Advanced Neuromodulation Systems, Inc. of Plano, Tex. Electrical pulses from pulse generator 150 are conducted through the conductors of lead body of stimulation lead(s) 160 and to the electrodes of lead(s) 160. The electrodes of stimulation lead(s) 160 can be implanted to apply the electrical pulses to tissue at any suitable location within the patient's body, such as within the epidural space, at a subcutaneous location, at a deep brain location, adjacent to cortex, adjacent to peripheral nerve tissue, etc.

As shown in FIG. 1, controller 110 comprises input controls 111 for receiving input from the user and display 112 for displaying information to the user. In some embodiments, display 112 may alternatively or additionally implement "touch-screen" functionality to permit the user to provide input by contacting various locations of display 112. Controller 110 comprises circuitry (not shown) for communication with pulse generator 150. The circuitry may comprise wireless communication circuitry for communicating with pulse generator 150 after implantation into a patient. The circuitry may additionally include circuitry for conducting communications via a wire connection (e.g., with a "trial stimulator"). Controller 110 further comprises a processor (not shown) for controlling the operations of controller 110 and memory (not shown) for storing data and software code. The memory need not be a single storage medium or device. As used herein, memory collectively refers to the various memory storage components of controller 110 (such as RAM, ROM, magnetic-media storage devices, solid-state storage, etc.). Also, controller 110 is depicted as a single device. In alternative embodiments, controller 110 could be implemented using software stored on a computer that is communicatively coupled to another device that conducts communications directly with pulse generator 150. The software stored in controller 110 enables the user to control implantable pulse generator 150 via display 112 and controls 111. Specifically, controller 110 may be employed by a clinician to program pulse generator 150.

When used to initially program implantable pulse generator 150 or to subsequently revise such programming, the clinician selects values for a number of programmable parameters in order to define the stimulation therapy to be delivered to a patient. The clinician may select perception amplitude, pulse amplitude, pulse width, pulse frequency, and electrode combinations. The clinician may also combine multiple sets of such stimulation parameters to define one or more "multi-stimulation set" programs, which are known in the art. The multi-stimulation set programs may allow pain in distinct regions of the body to be treated simultaneously, to permit differences in therapy to be delivered at different times of the day or for different patient activities, etc. Controller 110 preferably stores software code defining a number of interfaces to facilitate the selection of stimulation parameters and stimulation programs. The screens of the various interfaces are provided to the clinician via display 112 and the clinician inputs data relevant for the various screens using controls 111 and/or the touch-screen functionality of display 112. Upon selection of the respective stimulation parameters, controller 110 communicates the stimulation parameters to pulse generator 150 using suitable communication circuitry (preferably via a wireless RF signal) as is known in the art.

In preferred embodiments, controller 110 stores software code that permits a clinician to test a number of electrode combinations in an efficient manner. The software enables the clinician to shift a locus of stimulation longitudinally and laterally. For example, the clinician may attempt to relocate or move the locus of the stimulation along the spinal cord in order to change the perceived location of paresthesia in the patient. The clinician may relocate the locus of stimulation by selecting one or more graphical controls of a user interface. The software processes input from the user interface and automatically modifies the electrode polarities used to apply the stimulation pulses to nerve tissue in response to such input. As multiple movements (rostrally, caudally, left relative to midline, right relative to midline) are selected by the clinician, the software automatically applies different patterns of electrode polarities thereby providing respective incremental movements in the locus of stimulation.

FIGS. 2A-2F depict a stimulation lead in which different electrode combinations 201-206 are applied to electrodes of the lead to gradually shift the locus of stimulation longitudinally in a direction parallel to the longitudinal axis of the lead. Each combination of electrode combinations 201-206 defines a unique locus of stimulation, i.e., every combination applied to a common or base location produces a different locus of stimulation. Any suitable reference point may be selected for the base position. For example, a lower left most electrode of the combination could be selected as the base location. Alternatively, a particular position of each could be selected to serve as the base location. The selection of the base location need only be applied consistently between combinations of the set. The selection of a base location only effects when movement of the base location must occur when traversing through the electrodes of a stimulation lead.

FIG. 2A depicts electrode combination 201 in which the locus of stimulation is applied in a "lowest" longitudinal position relative to the other electrode combinations 202-206. Electrode combination 201 depicts cathode 201a present in the fourth electrode position (counting from the bottom of the lead) and anode 201b present in the fifth electrode position.

FIG. 2B depicts electrode combination 202 in which the locus of stimulation is shifted upwards relative to the locus of stimulation associated with combination 201. In combination 202, cathode 202a is present in the fourth electrode position and anodes 202b and 202c are present in the fifth and sixth electrode positions. The presence of an additional anode (anode 202c) shifts some of the return current flow to anode 202c, which would otherwise return to the pulse generator via anode 202b, thereby effecting a shift in the locus of stimulation.

FIG. 2C depicts electrode combination 203 where another "upward" shift in the locus of stimulation is present. Electrode combination 203 includes cathode 203a at the fifth electrode position and anodes 203b and 203c at the third and fourth electrode positions. FIGS. 2D-2F depict electrode combinations 204, 205, and 206 with further "upward" shifts in the locus of stimulation as defined by (i) cathode 204a and anode 204b; (ii) cathode 205a and anodes 204b and 204c; and (iii) cathode 206a and anode 206b.

Electrode combination 206 is the same as electrode combination 201 except that electrode combination 206 is shifted upward along the stimulation lead by one electrode position. That is, electrode combination 206 comprises cathode 206a at the fifth electrode position and anode 206b in the sixth electrode position while electrode combination 201 comprises cathode 201a at the fourth electrode position and anode 201b at the fifth electrode position. As can be appreciated, at this point, further upward shifts may occur from electrode combination 206 by utilizing the other electrode combinations 202-205 shifted up by one electrode position relative to the positions shown in FIGS. 2B-2E. The process of successively applying the electrode combinations and shifting the base position of the combinations may occur as many times as permitted by the number of available electrodes on the stimulation lead. Of course, the same process may occur to move the locus of stimulation down relative to the orientation of the stimulation lead.

Other electrode combinations may be employed according to alternative embodiments. FIGS. 3A-3H depict electrode combinations 301-308 in which seven unique electrode combinations are utilized to translate the locus of stimulation longitudinally along a column of electrodes. The set of seven unique electrode combinations 301-308 differ from the set of five combinations in FIGS. 2A-2E in that combinations 303 and 304 include a high impedance electrode state between a cathode and an anode to provide additional resolution to the incremental changes in the loci of stimulation within the set.

The locus of stimulation can also be shifted in a lateral manner by employing successive unique electrode combinations. FIGS. 4A-4H respectively depict electrode combinations 401-407 that gradually shift the locus of stimulation from left to right between two columns of electrodes formed by two stimulation leads.

Figure 5:
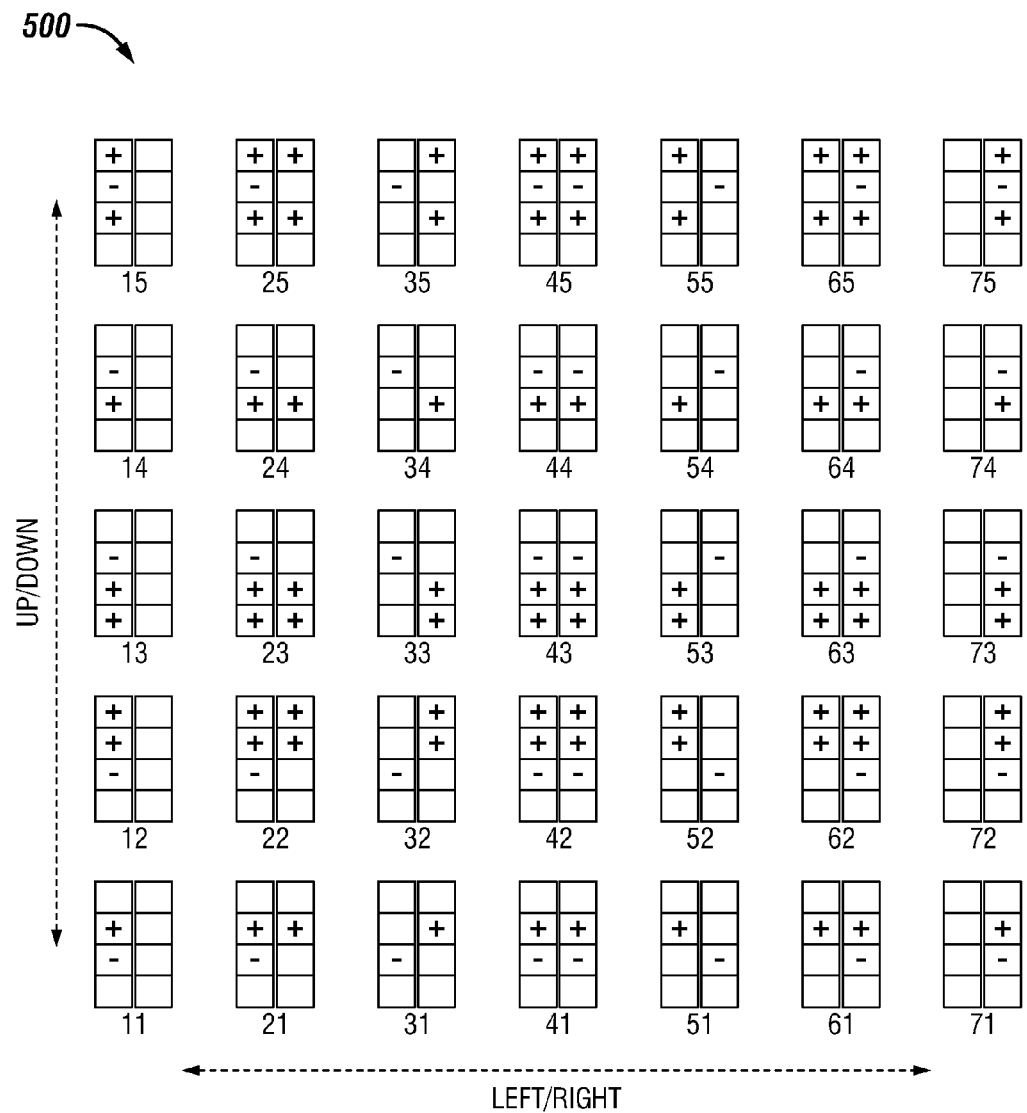
FIG. 5 depicts a set of electrode combinations that permit lateral and longitudinal movement of the locus of stimulation.

Representative embodiments preferably enable a clinician to move the locus of stimulation laterally and longitudinally along two adjacent columns of electrodes by defining a set of electrode combinations for such movement. FIG. 5 depicts set 500 of electrode combinations that permit lateral and longitudinal movement of the locus of stimulation. Set 500 defines specific positional states such that the clinician may maneuver stimulation in all four directions from state to state. As shown in FIG. 5, the electrode combinations of set 500 are indexed in a matrix type format. For each electrode combination shown in FIG. 5, the first numerical index refers to the lateral position of the locus of stimulation and the second numerical index refers to the longitudinal position of the locus of stimulation. The electrode combinations shown in FIG. 5 can be stored in controller 110 using any suitable data structure format and accessed by the software code of controller 110. Alternatively, the electrode combinations shown in FIG. 5 can be defined within the programmable logic of the software code of controller 110.

Suppose electrode combination (X,Y) is the current electrode combination. To move the locus of stimulation to the "right," electrode combination (X+1, Y) would be selected according to the indexing used in FIG. 5. To move the locus of the stimulation "up," electrode combination (X, Y+1) would be selected. When an electrode combination reaches the boundary of the matrix, a subsequent electrode combination can be selected from the other side of the matrix (and, if necessary, the base location for the combination moved). For example, if a downward movement is desired from electrode combination (1,1) electrode combination (1,5) would be selected.

Figure 6:
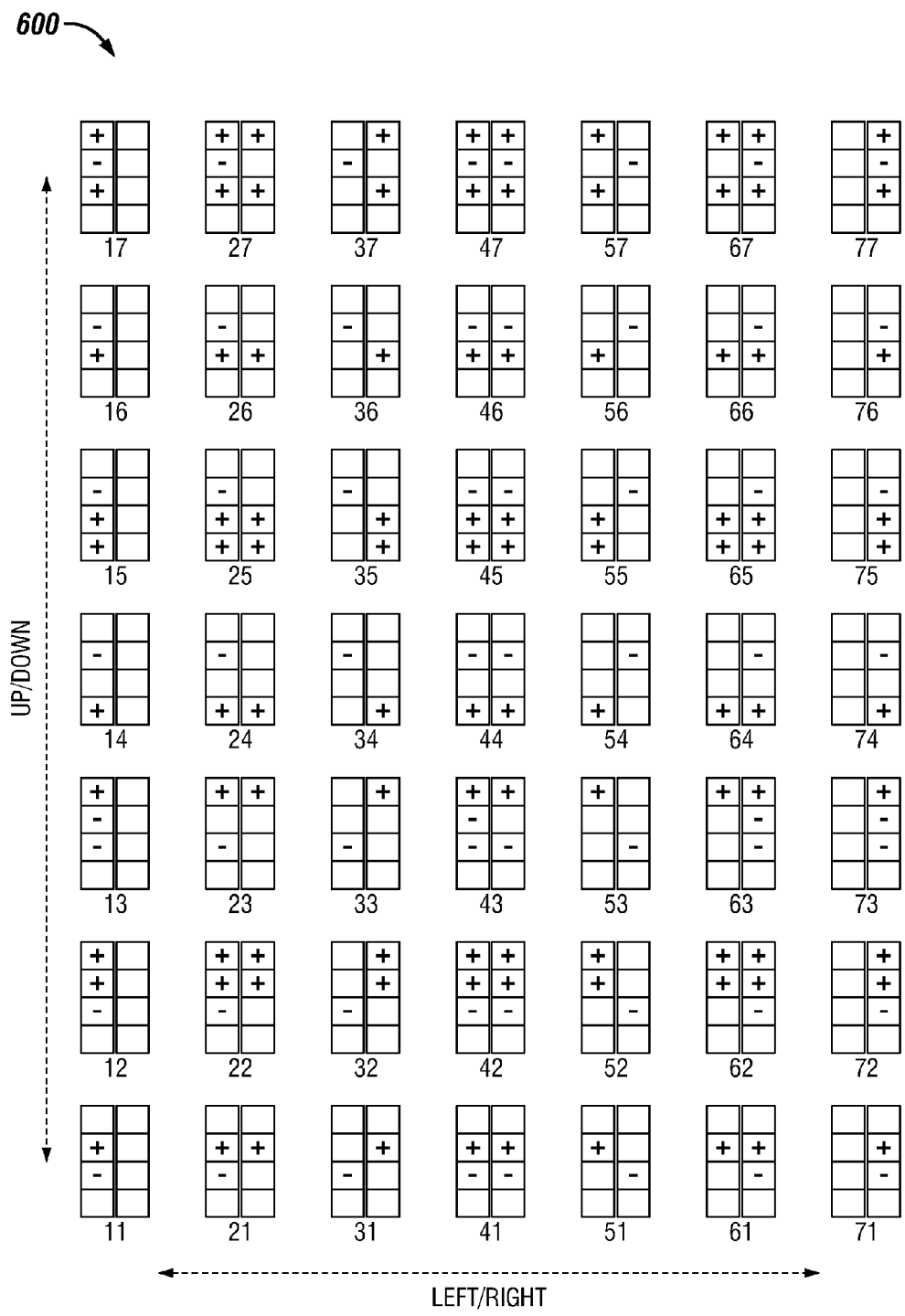
FIG. 6 depicts another set of electrode combinations that permit lateral and longitudinal movement of the locus of stimulation.

FIG. 6 depicts set 600 of electrode combinations that permit lateral and longitudinal movement of the locus of stimulation. Set 600 differs from set 500 in regard to the resolution in the shifts of the locus of stimulation. The greater amount of resolution is obtained by disposing high impedance electrode states between an anode and a cathode for certain electrode combinations.

Figure 7A:
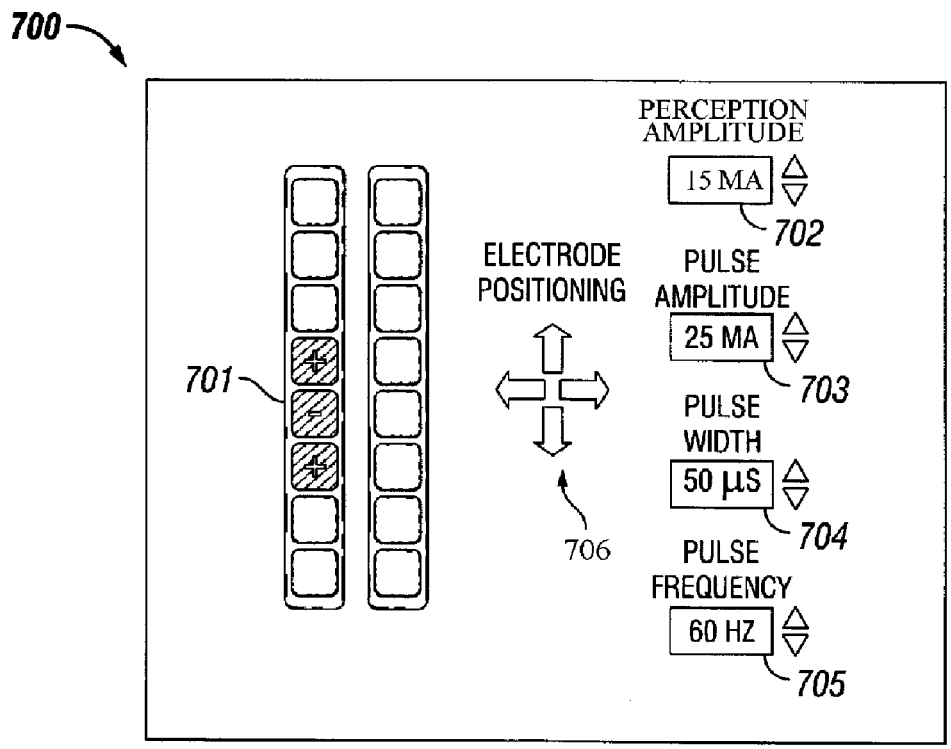
FIGS. 7a and 7b depict an example of interface 700 that permits a clinician to move the locus or loci of stimulation according to one representative embodiment.
Figure 7B:
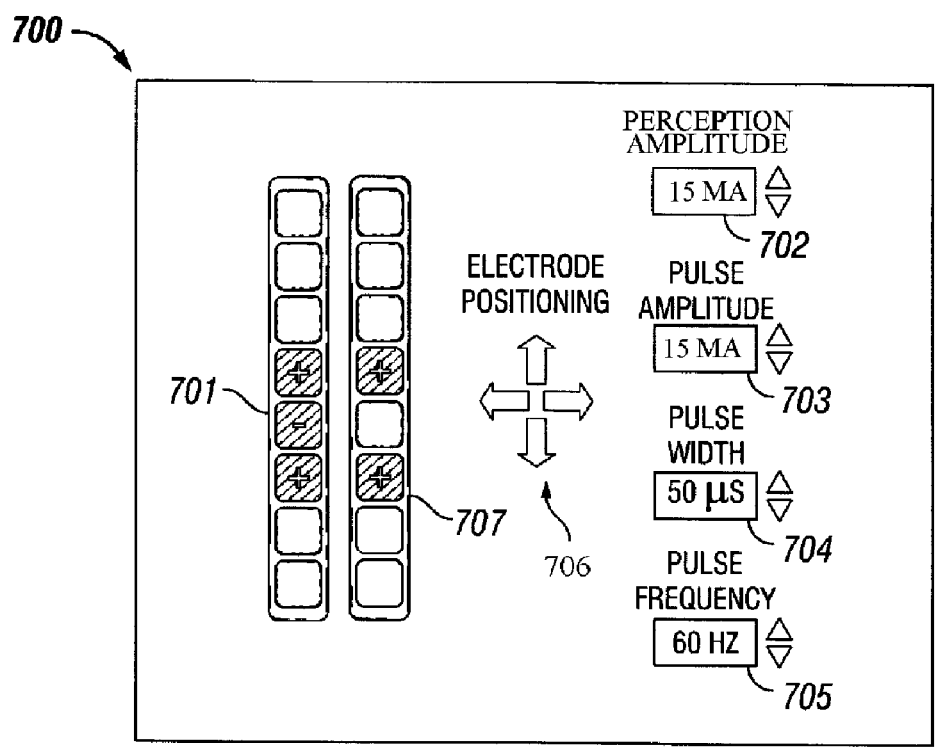

In preferred embodiments, software of controller 110 provides one or more interfaces that allow a clinician to move the locus of stimulation using a set of electrode combinations by selecting suitable graphical controls of the interface(s). FIGS. 7a and 7b depict an example interface 700 that permits a clinician to move the locus of stimulation according to one representative embodiment. Interface 700 includes a graphical control 701 that depicts the stimulation lead(s) available for use in applying stimulation to the patient. As shown, two eight-electrode percutaneous leads are available for use by the clinician. Preferably, interface 700 provides the ability to select from multiple leads and lead configurations (not shown). For example, in lieu of one or both the stimulation leads, interface 700 (at the selection of the clinician) could display electrodes of a paddle-style lead. Interface 700 may also comprise conventional graphical controls such as perception amplitude 702, amplitude control 703, pulse width control 704, and pulse frequency control 705.

As shown in FIGS. 7a and 7b, interface 700 comprises graphical control 706 that permits the clinician to not only adjust the stimulation parameters such as amplitude control 703, pulse width 704 and pulse frequency 705, but also move the locus of stimulation in a direction selected by the clinician, such as from the combination selected of electrodes selected in FIG. 7a 701 to the combination of electrodes as illustrated in FIG. 7b 701 and 707. Suitable software code of controller 110, executable on the processor of controller 110, responds to a selection of graphical control 706 by (i) determining the current electrode combination, (ii) determining a successive electrode combination from a set of possible electrode combinations using the current electrode state and the selected direction of movement, (iii) determining whether a change in the base position of the electrode position is necessary; (iv) determining whether electrodes are available (on the leads) for the successive electrode combination (i.e., whether the current electrode state is at perimeter location of the lead(s)); (v) automatically determining whether the set pulse amplitude 703 is higher than the set perception amplitude 702; (vi) decreasing the pulse amplitude 703 to be at least equal to the perception amplitude 702 if the determination is positive; and (vii) automatically applying the successive electrode combination if electrodes are available to accommodate the electrode combination.

Some embodiments are advantageous for programming a single-source stimulation system. As used herein, a single source-stimulation stimulation is a stimulation system that provides a single output pulse at any given time. Some embodiments are advantageous for such systems, because some embodiments provide a methodology for a clinician to incrementally shift the locus of stimulation between electrodes without requiring multiple simultaneous stimulation pulses.

In other embodiments, shifting of the locus of stimulation using different electrode combinations may be applied initially. After identifying multiple electrode combinations that possess loci of stimulation "close" to a desired loci, current "fractionalization" or "steering" may occur to further refine the locus of stimulation between such electrode combinations. For example, two closely-timed stimulation pulses on the identified electrode combinations may provide a time-domain summation to adjust the locus of stimulation. Alternatively, depending upon device capabilities, two simultaneous pulses may be applied to the identified electrode combinations. By utilizing different electrode combinations and, then, applying current fractionalization or steering, the programming process may occur in a more efficient manner. That is, the clinician may utilize the electrode combinations to more quickly identify an approximate "best" region for stimulation and then fine-tune stimulation within that region using pulse fractionalization or steering.

In another embodiment, shifting of the loci of stimulation for respective stim sets of a multi-stim set program may occur by incrementally shifting respective sets of electrode polarities pertaining to the respective stim sets of the program. As used herein, a "stim set" refers to a set of parameters which define a pulse to be generated and how the pulse is to be delivered. Each stim set may define a pulse amplitude, a pulse width, (optionally a pulse delay), an electrode combination, etc. The multi-stim set program includes multiple such stim sets. Execution of a multi-stim set program by a pulse generator involves repeatedly generating and delivering pulses in a successive manner for each stim set of the program. The generation of pulses in this manner may occur according to a program frequency.

It is further contemplate that a clinician may "click" on or otherwise select one of the combinations 701 and 707 and, thereby, select one of the stim sets for adjustment. Preferably, user interface 700 depicts the selection by modifying the display of one or more of the combinations (e.g., the "selected" combination being displayed using various colors, the non "selected" combination(s) being displayed using different colors, shaded colors, and/or hatching, etc.). Although not illustrated, it is contemplated that each of the stimulation leads depicted on interface 700 could each have associated therewith corresponding stimulation parameter controls. That is, there could be a separate controls for perception amplitude, pulse amplitude, pulse width and pulse frequency for each stimulation lead. Therefore, user interface 700 could modify the display of the pulse controls associated with the respective stim set upon such selection. Additionally the perception amplitude could be set for each of the stimulation leads, such that if the pulse amplitude of either or both of the stimulation leads exceeds the perception amplitude, upon a selection of a new electrode combination, the pulse amplitude of each stimulation lead could be individually decreased to the perception amplitude. After selection of a combination, the clinician may adjust the locus of stimulation for the respective stim set by using graphical control 706 as discussed above. The clinician may switch between the two combinations to move the respective loci of stimulation for the various stim sets as many times as deemed appropriate by the clinician.

Figure 8:
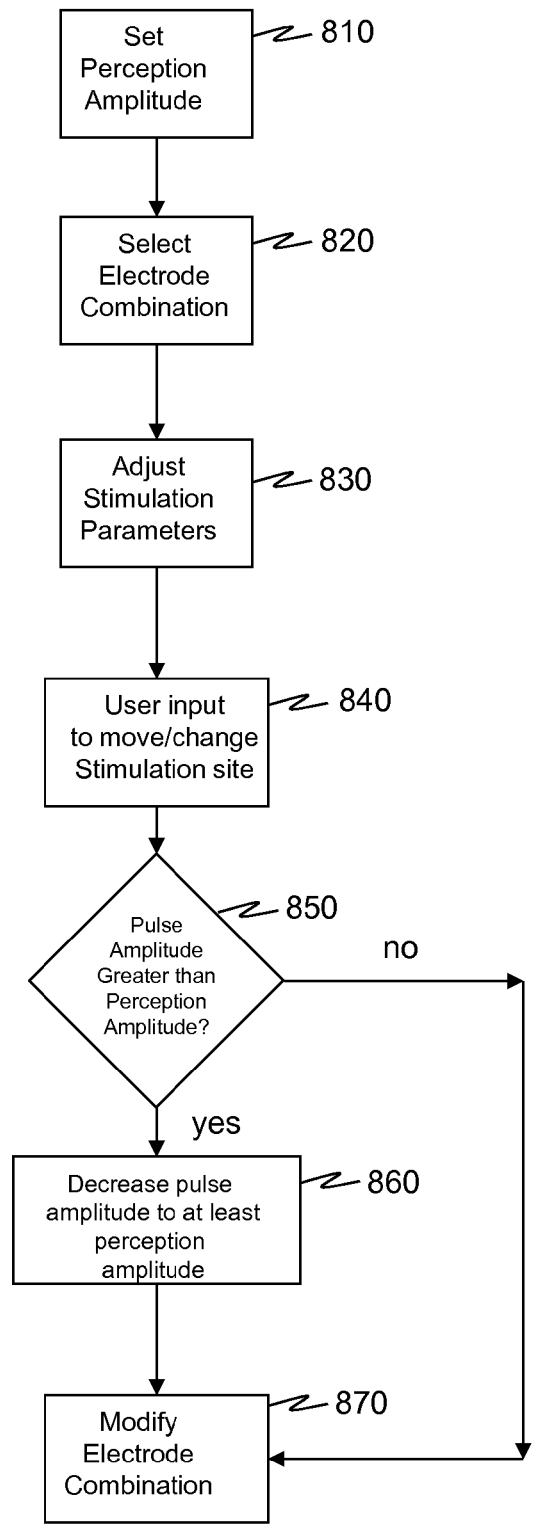
FIG. 8 depicts a flow chart of the steps utilized when a clinician attempts to move the locus or loci of stimulation according to one representative embodiment.

As illustrated in FIG. 8, the clinician will set a base line or perception amplitude 810 which is a value corresponding to at least a minimum pulse amplitude for which a patient can feel stimulation or paresthesia, or a pulse amplitude value for which the patient can comfortably feel the stimulation or paresthesia. A select electrode combination will be chosen 820 through which stimulation will be delivered to the patient. Once the electrode combination is selected, the stimulation parameters are selected or adjusted 830 and the stimulation is activated and delivered. As described herein, the stimulation parameters includes, but is not limited to, the pulse amplitude, pulse width and pulse frequency. For various reasons, such as to change the loci of the stimulation to optimize the efficacy to the patient, the clinician may choose to select a new combination of electrodes 840. Once the input to change the combination of electrodes is received, the controller determines if the current setting of value of the pulse amplitude is higher than the set perception amplitude 850 or alternatively is higher than a set value greater than the set perception amplitude. Such set value could represent a value corresponding to a particular user's stimulation comfort level. It the determination is positive, the pulse amplitude is decreased to select level, such as the set perception value 860 or a value corresponding to a particular user's stimulation comfort level. If the determination of 850 is negative or subsequent to the decreasing of the pulse amplitude 860, the electrode combination is modified 870.

As each of the electrodes on the stimulation lead is spaced apart with respect to each other, and therefore located in different positions within the patients, the effects of the stimulation delivered at each of the electrodes can vary from electrode to electrode. Ensuring that the pulse amplitude is automatically decreased to a select level or perception level before changing the electrode combinations facilitates faster programming and significantly reduces the delivery of stimulation pulses with too high of a pulse amplitude to the new set of electrodes.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

What is claimed:

1. A method for controlling stimulation pulses applied via a plurality of electrodes to tissue of a patient during the programming of a pulse generator using a controller device by a user, comprising:
   selecting one of a plurality of electrode combinations defined in the controller device;
   setting the value for a stimulation parameter for the stimulation pulses to be applied to the electrodes of the selected electrode combination;
   receiving input from the user to change the selected one of the plurality of electrode combinations to a different one of the plurality of electrode combinations;
   determining if the value for the stimulation parameter for the stimulation pulses is different than a predetermined value, and if the determination is positive, automatically changing the value for stimulation parameter for the stimulation pulses to be equal to the predetermined value; and
   if the determination is negative or subsequent to the changing of the value for the stimulation parameter for the stimulation pulses, changing the selected one of a plurality of electrode combinations to the different one of the plurality of electrode combinations.

2. The method of claim 1, determining a perception value corresponding to the minimum stimulation parameter for the stimulation pulses where the patient perceives stimulation.

3. The method of claim 2, wherein the predetermined value is the determined perception value.

4. The method of claim 3, wherein the stimulation parameter is the amplitude of the stimulation pulses.

5. The method of claim 1, determining a comfort value corresponding to the maximum stimulation parameter for the stimulation pulses where the patient is comfortable receiving stimulation.

6. The method of claim 5, wherein the determined value is the determined comfort value.

7. A method for controlling stimulation pulses applied via a plurality of electrodes to tissue of a patient during the programming of a pulse generator using a controller device by a user, comprising:
   selecting one of a plurality of electrode combinations defined in the controller device;
   setting the amplitude for the stimulation pulse to be applied to the electrodes of the selected electrode combination; and
   receiving input from the user to change the selected one of the plurality of electrode combinations to a different one of the plurality of electrode combinations;
   determining if the amplitude for the stimulation pulses is greater than a predetermined amplitude value, and if the determination is positive, automatically changing the amplitude of the stimulation pulses to be equal to or less than the select predetermined value; and
   if the determination is negative or subsequent to the changing the amplitude of the stimulation pulses, changing the selected one of a plurality of electrode combinations to the different one of the plurality of electrode combinations.

8. The method of claim 7, determining a perception value corresponding to the minimum amplitude for the stimulation pulses where the patient perceives stimulation.

9. The method of claim 8, wherein the predetermined value is the determined perception value.

10. The method of claim 7, determining a comfort value corresponding to the maximum stimulation parameter for the stimulation pulses where the patient is comfortable receiving stimulation.

11. The method of claim 10, wherein the determined value is the determined comfort value.

12. A method for controlling stimulation pulses delivered via a plurality of electrodes to tissue of a patient during the programming of a pulse generator using a controller device by a user, comprising:
   selecting a perception amplitude corresponding to the minimum amplitude of the stimulation pulses for which the patient can detect stimulation;
   selecting one of a plurality of electrode combinations defined in the controller device;
   setting the amplitude for the stimulation pulses to be applied to the electrodes of the selected electrode combination;
   receiving input from the user to change the selected one of the plurality of electrode combinations to a different one of the plurality of electrode combinations;
   determining if the amplitude for the stimulation pulses is greater than the perception amplitude, and if the determination is positive, automatically changing the amplitude of the stimulation pulse to less than or equal to the perception amplitude; and
   if the determination is negative or subsequent to the changing of the amplitude for the stimulation pulses to be less than or equal to the perception amplitude, changing the selected one of a plurality of electrode combinations to the different one of the plurality of electrode combinations.

* * * * *